United States Patent
Tang et al.

(10) Patent No.: US 8,703,975 B2
(45) Date of Patent: Apr. 22, 2014

(54) ARYL (ETHANOIC) PROPANOIC ACID ASCORBYL ESTER, PREPARATION METHOD THEREOF AND MEDICAMENT CONTAINING THE SAME

(75) Inventors: Luhong Tang, Jiangsu (CN); Ajuan Dai, Jiangsu (CN); Ze Wang, Jiangsu (CN); Yang Sun, Jiangsu (CN); Xinning Liu, Jiangsu (CN); Lingyan Xu, Jiangsu (CN); Xin Fang, Jiangsu (CN); Shuang Qiu, Jiangsu (CN); Yaqing Cao, Jiangsu (CN); Xiaomin Xu, Jiangsu (CN); Ruixia Jiang, Jiangsu (CN); Chao Wu, Jiangsu (CN)

(73) Assignees: Wuxi Hongrui Bio-Pharma-Tech Co., Ltd., Wuxi, Jiangsu (CN); Ning Tang, Wuxi, Jiangsu (CN)

( * ) Notice: Subject to any disclaimer, the term of this patent is extended or adjusted under 35 U.S.C. 154(b) by 0 days.

(21) Appl. No.: 13/320,101

(22) PCT Filed: Dec. 24, 2009

(86) PCT No.: PCT/CN2009/075994
§ 371 (c)(1),
(2), (4) Date: Jan. 21, 2012

(87) PCT Pub. No.: WO2010/130139
PCT Pub. Date: Nov. 18, 2010

(65) Prior Publication Data
US 2012/0115897 A1    May 10, 2012

(30) Foreign Application Priority Data
May 11, 2009  (CN) .......................... 2009 1 0026697

(51) Int. Cl.
*C07D 307/62*    (2006.01)
(52) U.S. Cl.
USPC ........................................................ 549/317
(58) Field of Classification Search
USPC .......................................................... 549/317
See application file for complete search history.

(56) References Cited

U.S. PATENT DOCUMENTS 7,074,826 B2 *  7/2006  Wechter et al. ............... 514/474

FOREIGN PATENT DOCUMENTS

WO    WO 2008017346     *  2/2008  ........... C07D 307/62
WO    PCT/CN2009/075994     4/2010

OTHER PUBLICATIONS

Stock et al. Rheumatol Int. 1991;11(4-5):199-202.*
Manfredini et al. J. Med. Chem. 2002, 45, 559-562.*

* cited by examiner

*Primary Examiner* — Nizal Chandrakumar
(74) *Attorney, Agent, or Firm* — Global IP Services; Tianhua Gu

(57) ABSTRACT

The present invention designs and synthesizes the ascorbyl ester derivatives of the aryl (ethanoic) propanoic acid non-steroidal anti-inflammatory medicaments, such as ibuprofen, ketoprofen and naproxen, and addition salt of the derivatives with pharmaceutical acid or pharmaceutical alkaline. The non-steroidal anti-inflammatory medicament which takes the ibuprofen as the representative is a common antipyretic analgesic medicament. The invention has remarkable antipyretic and analgesic effects and good safety except for anti-inflammatory effect, thus being not only suitable for adults, but also suitable for the elderly people, infants and children. The aryl (ethanoic) propanoic acid ascorbyl ester can be converted into ascorbyl ester derivatives and the addition salts of the derivatives with pharmaceutical acid or pharmaceutical alkaline, which can improve the water solubility thereof, facilitate intravenously administration, reduce the onset time, improve the bioavailability, reduce the stimulation effect to gastrointestinal tract, and enhance the penetrating capacity to hemato encephalic barrier, and can be used as a novel medicament to be applied for antiphlogistic, antipyresis, analgesia, treatment of arthritis, dysmenorrheal, multiple sclerosis, pneumonia cystic fibrosis and patent ductus arteriosus of premature infants, and prevention and treatment of cerebral apoplexy, hypoxic-ischemic brain damage, senile dementia and certain cancers.

6 Claims, No Drawings

ARYL (ETHANOIC) PROPANOIC ACID ASCORBYL ESTER, PREPARATION METHOD THEREOF AND MEDICAMENT CONTAINING THE SAME

CROSS REFERENCE TO RELATED PATENT APPLICATION

The present application is the US national stage of PCT/CN2009/075994 filed on Dec. 24, 2009, which claims the priority of the Chinese patent application No. 200910026697.9 filed on May 11, 2009, which application is incorporated herein by reference.

FIELD OF THE INVENTION

The present invention relates to new ester derivatives of non-steroidal anti-inflammatory medicament, a preparation method thereof and drug combinations containing the same, in particular to aryl (ethanoic) propanoic acid ascorbyl ester derivatives and its addition salts with pharmaceutical acid or pharmaceutical alkaline, preparation method thereof and drug combinations containing the same.

BACKGROUND ART

The non-steroidal anti-inflammatory drug represented by ibuprofen is one of the most successful antipyretic analgesic drugs in recent years. In addition to their anti-inflammatory effects, these drugs have significant analgesic, antipyretic effects and good safety, which are not only suitable for adults, but also can be applied for the elderly and infants. In foreign countries, ibuprofen has been main kind of antipyretic analgesic drug and widely used in non-prescription drugs (Over-the-counter, OTC) with high security requirements, which is considered as a variety with more development prospects than paracetamol and aspirin.

However, this kind of drugs always has lots of deficiencies, such as poor water solubility, gastrointestinal tract stimulation, slow absorption, low bioavailability, relatively slow onset, which bring a lot of inconvenience to children, the elderly and patients who can not swallow solid preparations.

In order to improve the problems of the solubility and the administration route, improve the product stability and bioavailability and speed up the onset velocity, the prior art has disclosed a large variety of improved technologies. CN99800474. disclosed a pharmaceutical preparation containing hydrosoluble ketoprofen salts and application thereof; CN00807563.8 disclosed a drinkable ibuprofen pharmaceutical suspension; CNO2109536.1 disclosed an ibuprofen triaazole nucleoside ester and preparation method and use thereof; CNO2110476.X disclosed a method for preparing clathrate of keto-brufen and beta-cyclodextrin or its derivatives; CNO2115459.7 disclosed a polycaprolactone-brufen composition and preparation method and use thereof; CNO2821502.8 disclosed ibuprofen salt emulsifiers and cream formulations containing the same; CNO3139116.8 disclosed an ibuprofen sugar conjugated product and preparation method and application thereof; CNO3144095.9 disclosed liquid soft capsule containing brufen and pseudoephedrine hydrochloride; CNO3145504.2 disclosed preparation method and use of mixture of arginine-burfenum; CNO3805774.3 disclosed ibuprofen solution for hard shell capsules; CN200410014369.4 disclosed a new method for preparing brufen arginine salts; CN200410021005.9 disclosed ibuprofen ester, pharmaceutically acceptable salt, and its preparing process and pharmaceutical composition; CN200410021590.2 disclosed eugenol ibuprofen ester medical compound and its preparation and preparation method; CN200510024043.4 disclosed ibuprofen sugar derivative and its preparing method and application; CN200510026269.8 disclosed a method for preparing 2-ary lactate, naprosyn and ibuprofen; CN200510040242.4 disclosed clean production method for fenoprofen calcium; CN200510060924.1 disclosed a water-dispersive nano-grade ibuprofen injecta and method for preparing the same; CN200510096990.4 disclosed preparation method of dexibuprofen amino acid salt and application thereof; CN200610038794.6 disclosed soft capsule composition containing zine gluconate, ibuprofen and chlorphenamine maleate; CN200610044134.9 disclosed injection containing ibuprofen and preparation method thereof; CN200610044528.4 disclosed injection containing ketoprofen and preparation method thereof; CN200610090025.0 disclosed an ibuprofen arginine compound medicament for children; CN200610129620.0 disclosed a method for preparing arginine ibuprofen salt; CN200610130587.3 disclosed oral dissolved brufen tablet and its preparing method; CN200610170923.7 disclosed infusion preparation of ibuprofen and preparation method thereof; CN200680001752.3 disclosed syrup composition comprising dexibupropen as active ingredient and preparation method thereof; CN200680016935.2 disclosed solubilized ibuprofen; CN200710004659.4 disclosed dexibuprofen pharmaceutical composition with improved digestion performance and method for preparing the same; CN200810000637.5 disclosed ibuprofen amino acid salt injection and preparation method thereof; CN200810102110.3 disclosed method for preparing brufen arginine salt; CN200810105086.9 disclosed amino acid salt of (S)-ibuprofen and medicinal composition thereof.

However, the ibuprofen non-steroidal anti-inflammatory drugs are combined with ascorbic acid and converted into ascorbic acid esters. The research of using the salts formed by ibuprofen non-steroidal anti-inflammatory drugs with pharmaceutically acceptable acid or alkali to improve the soluble performance, onset speed, bioavailability and blood-brain barrier penetration performance has not been in any reports.

SUMMARY OF THE INVENTION

The present invention invented a new variety of ester derivatives of ibuprofen non-steroidal anti-inflammatory drugs, ascorbic acid esters of ibuprofen non-steroidal anti-inflammatory drugs, and its addition of salts with pharmaceutical acid or pharmaceutical alkaline. The compound of the present invention is novel because of its new structure, especially the compound of the present invention has valuable pharmacokinetic properties, such as good solubility, bioavailability, rapid onset and strong blood-brain barrier penetration performance, and valuable pharmacological properties that can be used for treating patent ductus arteriosus of premature infants, cerebral apoplexy, ischemic brain injury, Alzheimer's disease and certain cancers.

In particular, the present invention relates to compound of formula (I), its enantiomers, racemic mixtures and non-enantiomers thereof, and its addition salts with pharmaceutically acceptable acid or alkali:

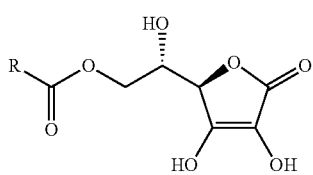

(I)

wherein R represents:

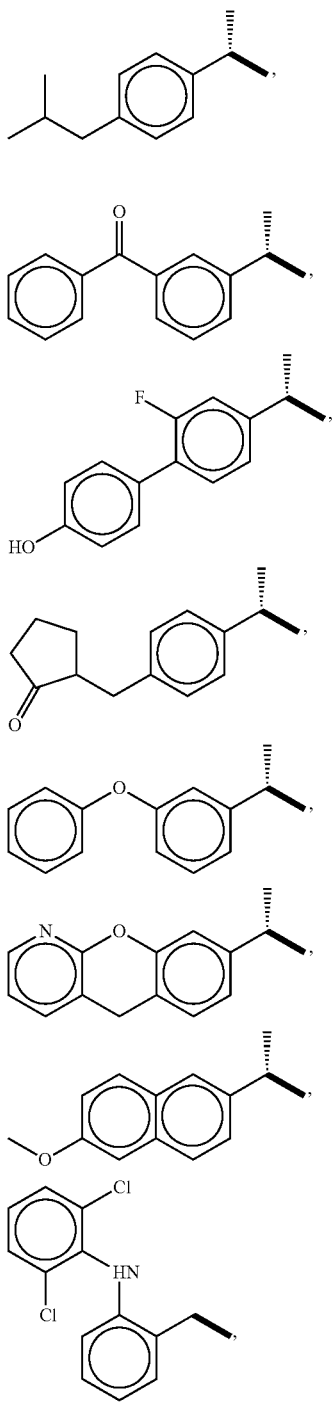

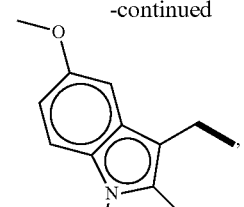

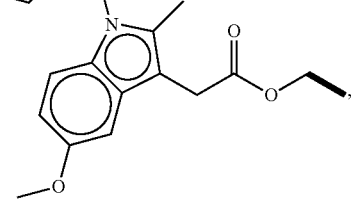

or

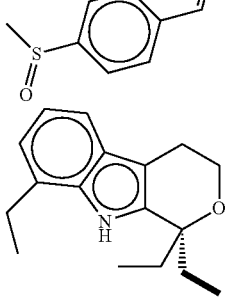

The pharmaceutically acceptable acid includes, but not limiting in any way, phosphoric acid, trimetaphosphoric acid, tripolyphosphoric acid, etc.

The pharmaceutically acceptable alkali includes, but not limiting in any way, sodium hydroxide, potassium hydroxide, ammonia, zinc hydroxide, magnesium hydroxide, calcium hydroxide, etc.

The preferred compounds of the present invention include the following compounds:

L-ascorbic acid-6-O—(S)-ibuprofen ester;
L-ascorbic acid-6-O—(S)-ketoprofen ester;
L-ascorbic acid-6-O—(S)-naproxen ester; and
L-ascorbic acid-6-O—(S)-indomethacin ester.

The enantiomers, racemic mixtures and non-enantiomers of the preferred compounds in the present invention and its addition salts with pharmaceutically acceptable acid or alkali also constitutes an important part of the present invention.

The present invention also relates to a method for preparing compound of formula (I), which is characterized in that aryl (ethanoic) propanoic acid ascorbyl ester is prepared according to the following reaction equation through an esterification reaction of L-ascorbic acid as substrate with another substrate compound of formula (II) in special reaction system under the catalysis of lipase:

RCOOH (II)

wherein R is defined as above:

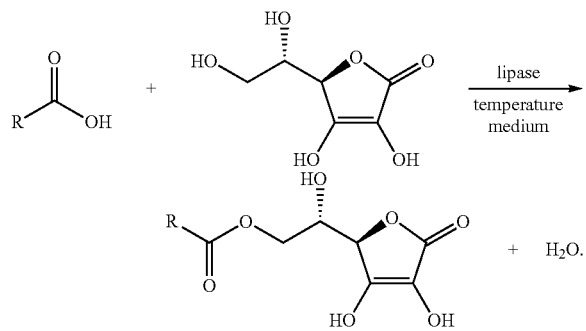

The method is composed of the following steps:

(1) 6-hydroxy of L-ascorbic acid is reacted with the compound of formula (II) under catalysis of lipase in special reaction system to give L-ascorbic acid-6-O-ester, thus obtaining equilibrium mixture consisting of reactant L-ascorbic acid, compound of formula (II), reaction product L-ascorbic acid-6-O-ester and water;

(2) said equilibrium mixture is separated and extracted to obtain the target product, compound of formula (I).

We found that the lipase used as catalyst can be commercially available varieties of common lipase, such as Novozym435, pancreatic lipase; the reaction medium can be acetone, tert-butanol(2-methyl-2-propanol), tertiary amyl alcohol(2-methyl-2-butanol), hexane, octane, cyclohexane, benzene, toluene, xylene, ionic liquid, supercritical fluid and any other available liquid or fluid which can catalyze the reaction for lipase; the esterification reaction can be carried out at the reaction temperature of −30 to 200° C., under the reaction pressure of 0.0001 to 0.5 MPa; the separation and extraction, including extraction, crystallization, column chromatography, solvent recovery and any other necessary common operation process through which pure substance can be obtained from the reaction mixture, should be carried out at the temperature of −30 to 200° C., under the pressure of 0.0001 to 3.5 MPa.

The compounds of formula (I) have important pharmacokinetic properties and pharmacological properties. Their addition salts with pharmaceutically acceptable acid or alkali have good water solubility, excellent bioavailability and blood-brain barrier penetration performance, rapid onset and low low effective dose, which can be act in central nervous system and cerebrovascular, therefore these addition salts can used in medical for antiphlogistic, antipyresis, analgesia, treatment of arthritis, dysmenorrheal, multiple sclerosis, pneumonia cystic fibrosis, patent ductus arteriosus of premature infants, prevention and treatment of cerebral apoplexy, hypoxic-ischemic brain damage, senile dementia and certain cancers.

The present invention also relates to a compound of formula (I), its enantiomers and its addition salts with pharmaceutically acceptable acid or alkali or pharmaceutical composition with one or more inert, non-toxic excipients or carriers.

The pharmaceutical compositions of the present invention especially include those compositions suitable for administration per oral, parenteral, nasal, rectal, tongue, eyes or breath, in particular tablet or sugar-coated pill, sublingual tablet, cachet, paquet, gelatin capsule, glossette, pastille, suppository, creams, oil ointment, gel for skin, injectable or drinkable preparation, aerosols agent, eye drop or nasal drop.

The effective dose is determined according to patient's age and weight, administration route, property of treated indications and any related treatment, which ranges from 0.1 mg/day to 800 mg/day, and is dosed once or divided into multiple doses.

DETAILED DESCRIPTION OF THE PREFERRED EMBODIMENTS

In order to better understand the present invention, the present invention is illustrated through the following embodiments, but not limiting the contents of the present invention.

Embodiment 1

L-Ascorbic Acid-6-O—(S)-Ibuprofen Ester

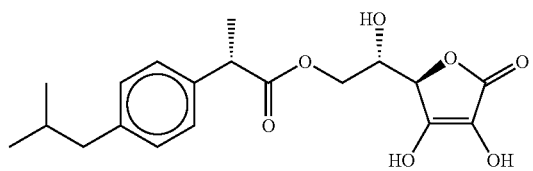

0.85 g of L-ascorbic acid and 60 ml of 25% (w/v) (S)-ibuprofen tertiary amyl alcohol solution were added into a 500 ml conical flask with stopper, placed in a gas bath constant-temperature oscillator and heated to 55° C., and then added with 1 g of Novozym 435. The system was reacted at the shaking speed of 200 rpm for 12 hrs, added with 1 g of molecular sieve A4, and continued to shake under the same conditions for 12 hrs to obtain the reaction mixture.

The hot mixture was immediately filtered to eliminate unreacted reactants and enzymes to give clear filtrate. The filtrate was washed with equivalent amount of saturated salt water for 4-5 times and the tertiary amyl alcohol was removed through rotary evaporation under vacuum condition at 49° C. to give the solid. The resulted solid was weighed and added with cyclohexane at the amount of 10%, slightly heated in water bath at 45° C. and fully stirred to dissolve, and then placed into 4° C. refrigerator overnight to give crystal. The mixture was filtered and the filter cake was washed with cyclohexane for several times, reclaimed and dried at room temperature to obtain the title compound.

Melting point: 145 to 146° C.

Trace element analysis:

Calculated value %: C, 62.64; H, 6.63

Measured value %: C, 62.68; H, 6.69

Embodiment 2

Structure Determination of the Title Compound in Embodiment 1

Its structure was determined and the resulting product was L-ascorbic acid-6-O—(S)-ibuprofen ester. The characteristical physical, chemical and structural analysis parameters are as follows:

m.p. 145~146° C.

$[\alpha]_D=+21.8°$ (c=0.00232 g/ml, CH$_3$OH). 0.1003 g, 50 ml (c=0.00611 g/ml, CH$_3$OH)

IR (KBr, cm$^{-1}$): 3395.52, 3222.26, 3022.03, 2954.93, 2876.59, 2954.93, 2876.59, 1761.60, 1709.72, 1665.92, 1665.92, 1510.01, 1463.13, 1382.85

$^1$H NMR (400 MHz, CD$_3$OD): 7.20 (d, 2H), 7.11 (d, 2H), 4.39 (d, 1H), 4.12 (t, 2H), 3.99 (t, 1H), 3.75 (t, 1H), 2.44 (d, 2H), 1.82 (t, 1H), 1.47 (d, 3H), 0.88 (t, 6H)

$^{13}$C NMR (400 MHz, CD$_3$OD): δ(ppm) 18.8533 (C$_8$), 22.8453, 22.7906 (C$_1$+C$_{1'}$), 31.6083 (C$_3$), 46.3302, 46.1564 (C$_9$+C$_2$), 65.7436 (C$_{12}$), 67.7221 (C$_{11}$), 76.8915 (C$_{13}$), 120.1202 (C$_{15}$), 128.4167 (C$_5$+C$_{5'}$), 130.5936 (C$_6$+C$_{6'}$), 141.9723, 139.4376 (C$_7$+C$_4$), 154.1888 (C$_{14}$), 173.2871, 176.1047 (C$_{10}$+C$_{16}$)

MS(m/z): 365.4 (M+H$^+$), 363.3 (M−1).

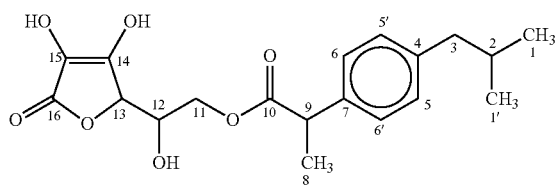

Solubility: soluble in methanol, ethanol, propylene glycol, and insoluble in chloroform, cyclohexane, water.

Embodiment 3

L-Ascorbic Acid-6-O-Ibuprofen Ester

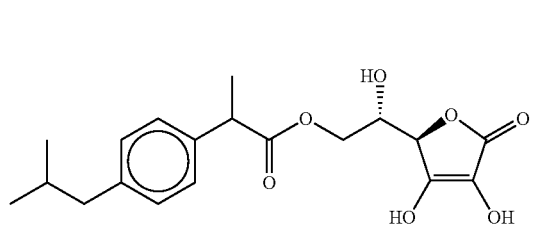

The method was the same as that in embodiment 1, in which (S)-ibuprofen was substituted by racemic ibuprofen.

Melting point: 145~146° C.
Trace element analysis:
Calculated value %: C, 62.64; H, 6.63
Measured value %: C, 62.65; H, 6.70
$[\alpha]_D=0°$ (c=0.00611 g/ml, CH$_3$OH)

Embodiment 4

L-Ascorbic Acid-6-O—(S)-Ketoprofen Ester

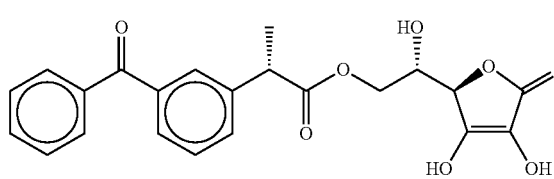

The method was the same as that in embodiment 1, in which (S)-ibuprofen was substituted by (S)-ketoprofen.

Melting point: 165~166° C.
Trace element analysis:
Calculated value %: C, 64.07; H, 4.88
Measured value %: C, 64.15; H, 4.90
$[\alpha]_D=+20.3°$ (c=0.00311 g/ml, CH$_3$OH)

Embodiment 5

L-Ascorbic Acid-6-O—(S)-Loxoprofen Ester

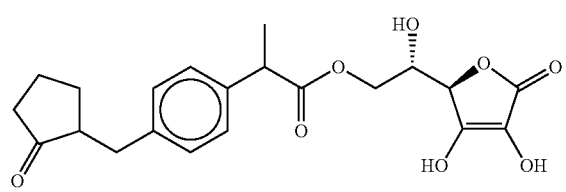

The method was the same as that in embodiment 1, in which (S)-ibuprofen was substituted by racemic loxoprofen.

Melting point: 168~169° C.
Trace element analysis:
Calculated value %: C, 62.36; H, 5.98
Measured value %: C, 62.45; H, 6.13
$[\alpha]_D=0°$ (c=0.00231 g/ml, CH$_3$OH)

Embodiment 6

L-Ascorbic Acid-6-O—(S)-Pranoprofen Ester

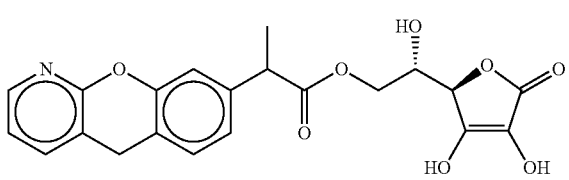

The method was the same as that in embodiment 1, in which (S)-ibuprofen was substituted by racemic pranoprofen.

Melting point: 198~199° C.
Trace element analysis:
Calculated value %: C, 61.01; H, 4.63; N, 3.39
Measured value %: C, 61.05; H, 4.73; N, 3.41
$[\alpha]_D=0°$ (c=0.00231 g/ml, CH$_3$OH)

Embodiment 7

L-Ascorbic Acid-6-O—(S)-Naproxen Ester

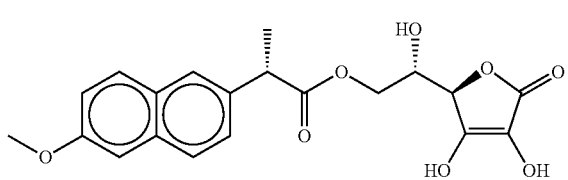

The method was the same as that in embodiment 1, in which (S)-ibuprofen was substituted by (S)-naproxen.

Melting point: 215~216° C.
Trace element analysis:
Calculated value %: C, 61.85; H, 5.15

Measured value %: C, 61.87; H, 5.18
$[α]_D$=+18.5° (c=0.00511 g/ml, $CH_3OH$)

Embodiment 8

L-Ascorbic Acid-6-O-Etodolac Ester

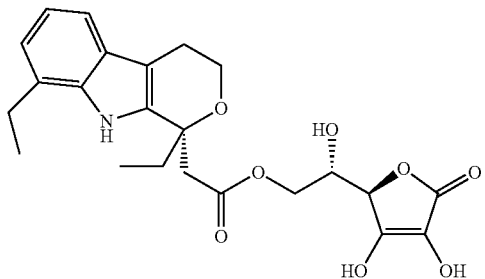 [SMILES: CCc1cccc2c3c([nH]c12)[C@@](CC)(CC(=O)OC[C@H](O)[C@H]1OC(=O)C(O)=C1O)OCC3]

The method was the same as that in embodiment 1, in which (S)-ibuprofen was substituted by etodolac.
Melting point: 218~219° C.
Trace element analysis:
Calculated value %: C, 62.01; H, 6.06; N, 3.14
Measured value %: C, 62.07; H, 6.10; N, 3.21
$[α]_D$=0° (c=0.00201 g/ml, $CH_3OH$)

Embodiment 9

Preparation of Sodium Salt L-Ascorbic Acid-6-O—(S)-Ibuprofen Ester

Under the conditions of continuous stirring, 100 ml methanol solution of 0.05 mol/L L-ascorbic acid-6-O—(S)-ibuprofen ester was taken and mixed with equivalent volume and equivalent molar concentration of sodium hydroxide methanol solution, and placed into a rotary evaporator and concentrated under vacuum to one-third of the original volume, and the resulting solution was standed overnight at 4° C. and filtrated to give 1.8 g of the title compound.
The solubility in water was determined as 12.8 g.

Embodiment 10

Sodium Salt L-Ascorbic Acid-6-O—(S)-Ibuprofen Ester: Arteriovenous Loop Thrombus Normal rats, half male and half female, were randomly grouped according to table 1. The administration group was given water solution of Sodium Salt L-ascorbic acid-6-O—(S)-ibuprofen ester (pH 7.4) by gavage and the control group was given equivalent pH normal saline for continuous 3 days. The rat was intraperitoneally injected with 350 mg of 8% chloral hydrate per kg for anesthesia 1 h after the last administration, and then fixed in the supine position to separate the right common carotid artery and the left external jugular vein. An early weighed No. 7 operation line (about 8 cm long) was placed in the middle of a 10 cm long polyethylene tube, and then the tube was filled with normal saline and both ends of the tube were connected with an intubation filled with heparin (about 3 cm long), in which one end was inserted into the jugular vein, and the other end was inserted into the common carotid artery. After opening the artery clip, the in vitro loop flow was formed. The blood flow was interrupted after 15 min followed by quickly taking the thrombus and weighing. The weight minus the weight of silk thread gave the wet weight of thrombus.
Thrombus inhibition rate: (thrombus wet weight in the control group−thrombus wet weight in the treatment group)/thrombus wet weight in the control group
Statistical analysis: the experimental data was represented as $\bar{x}±s$, and the significance of the differences was determined with one-factor analysis of variance. t represented t-test results between the control group and the Sodium Salt L-ascorbic acid-6-O—(S)-ibuprofen ester.

TABLE 1

| Thrombus inhibition rate | | | | | |
|---|---|---|---|---|---|
| Groups | n | Dose mg·$kg^{-1}$ | thrombus wet weight/body weight × 100 | Thrombus inhibition rate/% | t |
| Control | 4 | — | 11.914 ± 0.241 | — | — |
| Sodium Salt L-ascorbic acid-6-O—(S)-ibuprofen ester | 8 | 5.4 | 10.372 ± 0.801** | 12.9 | 0.003 |

Variance analysis, P < 0.05; compared with the control group, **P < 0.01, *P < 0.05.

From table 1, we can find that there was significant difference between the thrombus inhibition rates in the Sodium Salt L-ascorbic acid-6-O—(S)-ibuprofen ester group and the control group (P<0.01), and Sodium Salt L-ascorbic acid-6-O—(S)-ibuprofen ester can inhibit the thrombosis and enhance anti-coagulation function. The thrombus inhibition rate of Sodium Salt L-ascorbic acid-6-O—(S)-ibuprofen ester was up to 12.9%.

Embodiment 11

Tablets with Each Piece Containing 300 mg of L-Ascorbic Acid-6-O—(S)-Ibuprofen Ester

| Formulation for preparing 1000 tablets: | |
|---|---|
| L-ascorbic acid-6-O—(S)-ibuprofen ester | 300 g |
| Wheat starch | 300 g |
| Potato starch | 300 g |
| Lactose | 1000 g |
| Magnesium stearate | 50 g |
| Silica | 20 g |
| Hydroxypropyl cellulose | 30 g |

Embodiment 12

Injection with Each Injection Containing 200 Mg of Sodium L-Ascorbic Acid-6-O—(S)-Ibuprofen Ester

| Formulation for preparing 1000 injections: | |
|---|---|
| Sodium L-ascorbic acid-6-O—(S)-ibuprofen ester | 200 g |
| Lactose | 200 g |

What is claimed is:
1. A compound of formula (I), and addition salts thereof with pharmaceutically acceptable acid or alkali:

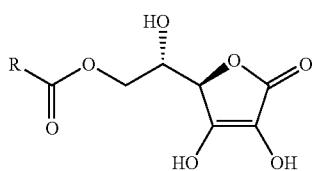

Wherein R represents

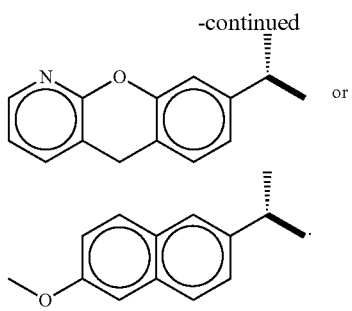

2. The compound of formula (I) according to claim 1, which is L-ascorbic acid-6-O—(S)-Ibuprofen ester, and addition salts thereof with pharmaceutically acceptable acid or alkali.

3. A pharmaceutical composition, which contains at least one compound according to claim 1 as active ingredient or combination of the compound with one or more inert, non-toxic pharmaceutically acceptable excipient or carrier.

4. The pharmaceutical composition according to claim 3, which is used for antiphlogistic, antipyresis, analgesia, treatment of arthritis, dysmenorrheal, multiple sclerosis, pneumonia cystic fibrosis, patent ductus arteriosus of premature infants, prevention and treatment of cerebral apoplexy, hypoxic-ischemic brain damage, senile dementia and certain cancers.

5. A pharmaceutical composition, which contains at least one compound according to claim 2 as active ingredient or combination of the compound with one or more inert, non-toxic pharmaceutically acceptable excipient or carrier.

6. The pharmaceutical composition according to claim 5, which is used for antiphlogistic, antipyresis, analgesia, treatment of arthritis, dysmenorrheal, multiple sclerosis, pneumonia cystic fibrosis, patent ductus arteriosus of premature infants, prevention and treatment of cerebral apoplexy, hypoxic-ischemic brain damage, senile dementia and certain cancers.

* * * * *